United States Patent [19]

Greenwood

[11] 4,199,897
[45] Apr. 29, 1980

[54] METHOD FOR INDUCING EARLY FLOWERING ON YOUNG FOREST TREES

[75] Inventor: Michael S. Greenwood, Hot Springs, Ark.

[73] Assignee: Weyerhaeuser Company, Tacoma, Wash.

[21] Appl. No.: 910,990

[22] Filed: May 30, 1978

[51] Int. Cl.² .............................................. A01H 1/00
[52] U.S. Cl. ................................... 47/58; 47/DIG. 1
[58] Field of Search ................ 47/1, 1.41, 58, DIG. 1, 47/DIG. 3, DIG. 6

[56] References Cited

PUBLICATIONS

Greenwood, Michael S. 1977 "Flower Stimulation Techniques for 'Loblolly' Pine" in *Proceedings Third World Consultation on Forest Tree Breeding* Canberra, pp. 1–10.
Jackson, D. I. and G. B. Sweet 1971 "Flower Initiation in Temperate Woody Plants" *Horticultural Abstracts*, 42, pp. 9–24.
Jackson, D. I. and G. B. Sweet (Undated) "Flower Determination in Temperate Woody Plants" New Zealand Forest Service, Reprint No. 508, pp. 1–59.
Romberger, J. A. and R. A. Gregory 1974 "Analytical Morphogenesis and Physiology of Flowering in Trees" in *Proceedings Third North American Forest Biology Workshop*, Colorado State University, Fort Collins, pp. 132–147.
Sachs, R. M. 1977 "Nutrient Diversion: An Hypothesis to Explain the Chemical Control of Flowering" *Horticultural Science* 12, No. 3, pp. 220–222.
Zimmerman, Richard H. 1972 "Juvenility and Flowering in Woody Plants: A Review" *Hortscience*, 7 No. 5, pp. 447–455.
Zimmerman, Richard H. 1973 "Juvenility and Flowering of Fruit Trees" *ACTA Horticulturae*, 34, pp. 139–142.
Downs, R. J. et al. (1958) "Effects of Photoperiod and Kind of Supplemental Light on Vegetative Growth of Pines" *Forest Science* vol. 4, No. 3 (Sep.), pp. 185–195.
Hanover, James W. (1976) "Accelerated-Optimal-Growth: A New Concept in Tree Production" *American Nurseryman* vol. Unknown (Nov.), pp. 12, 13, 58, 59, 61 and 62.
Pharis, R. P. (1976) "Chapter 13—Manipulation of Flowering in Conifers Through the Use of Plant Hormones" Proceedings in Life Sciences—Modern Methods in Forest Genetics (Ed. Miksche) Pub. Springer-Verlag, N.Y., pp. 265–282.

*Primary Examiner*—E. H. Eickholt
*Assistant Examiner*—James R. Feyrer

[57] ABSTRACT

This invention is a method for inducing early flowering in juvenile phase softwood tree species, particularly those within the genus Pinus. This is accomplished by reducing temperature and photoperiod conditions, during a time in which growth would otherwise be active, so that the tree falls into a quiescent or resting phase short of full dormancy. Early bud set occurs, yet active bud development continues. The resting phase is maintained for a sufficient time for sexual buds to differentiate and form. The plant is then allowed to resume normal growth and flowering. By this method both male and female flowers have been produced in grafted loblolly pine scions as young as three years from seed. Normally little or no flowering occurs in this species until trees are from 15 to 18 years old.

7 Claims, 1 Drawing Figure

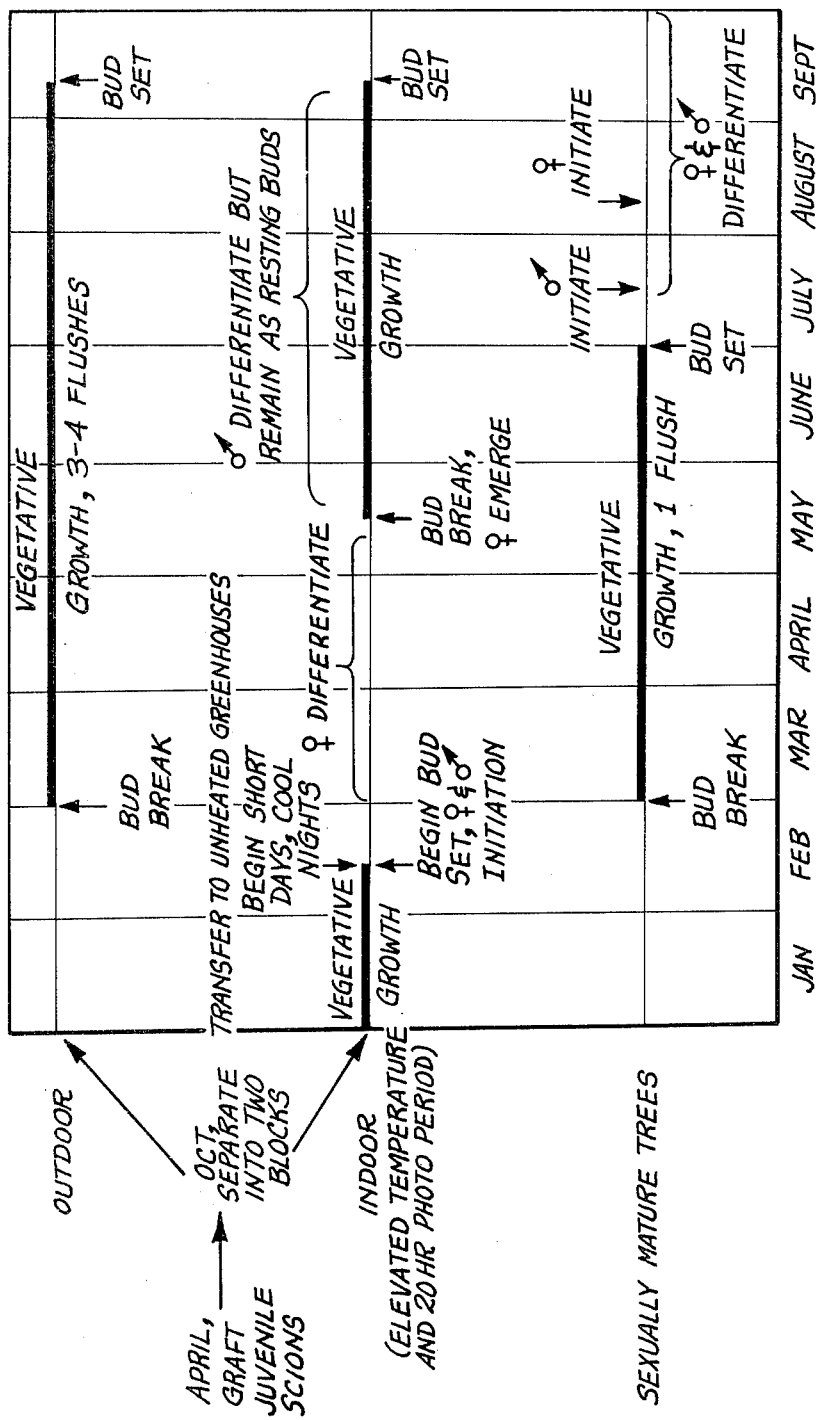

METHOD FOR INDUCING EARLY FLOWERING ON YOUNG FOREST TREES

BACKGROUND OF THE INVENTION

This invention relates generally to the production of improved strains of forest trees and more particularly to a method for inducing juvenile flowering in certain gymnosperms, especially those within the family Pinaceae.

For many foward-looking land managers within the forest products industry have been reforesting cut-over land in order to produce a new crop of timber or pulp wood trees. In the early days of the program, it was customary to leave individual mature trees, or a block of trees, uncut to provide a seed source for the following generation. While generally successful, this method has a number of serious limitations. Many desirable species of trees produce good seed crops only at infrequent and undependable intervals. Douglas-fir, *Pseudotsuga menziesii*, and loblolly pine, *Pinus taeda* are two such examples. Good cone crops typically occur every five to seven years. In this period of time it is not uncommon for competing brush or less desirable tree species to take over the land. The result of depending entirely on natural reseeding was often to have large areas of land which were poorly stocked in the preferred species.

One adverse effect of depending on natural seeding was often recognized and unintended. Quite often the remaining seed trees were chosen because they were of a form or condition that caused them to be of lower economic value than the surrounding trees in the stand. No thought was given to the possibility that the poor form might be a heritable genetic characteristic which would be transmitted to a predominant number of trees in the succeeding forest. Rarely was there any genetic gain from stand to stand. Much more often it was neutral and very frequently is was actually dysgenic for the reasons just given.

Even in the first quarter of the present century, a few progressive foresters maintained small nurseries to supply seedlings for reforestation. Unfortunately, at that time the effort was not widespread because of adverse economic factors and because so few people had vision to realize that the great stands of virgin timber in the world's forests would not last forever. It soon became painfully apparent that this was not the case. About the same time, forest managers began to see the limitations of natural restocking. Late in the second quarter of the century nurseries began to supply millions of tree seedlings which were hand planted to restock cut-over forest land. Other techniques, such as aerial reseeding, were also brought into play to minimize the time lag between harvesting one forest crop and beginning to grow another one.

For much of the time that tree nurseries have been in existence, they have depended on wild seed for production of seedlings. Collection of the cones of various evergreens became an important source of income for many rural people. In good seed years, more than adequate seed was collected for the next year's needs. The balance would be put into cold storage for subsequent years, thus minimizing somewhat the effect of the cyclic nature of seed production.

Wild seed is drawn from an enormously varied gene pool. It was not long before foresters began to recognize that some seedlings grew far better in localized enviornments than others. In the Douglas-fir region, for example, it was found to be important to plant seedlings at the same approximate altitude from which the seed had been obtained. Soon it was realized that many other tree characteristics were heritable. While these traits varied from species to species, among them might be mentioned growth rates, the tendency to have straight or crooked stems, wood density, light vs. heavy limbs, etc. Nursery managers thus began searching their forest for wild trees that would excel in one or more desirable characteristics. The principle trait sought was rapid growth rate. By restocking with trees having faster growth, years could be trimmed from the crop rotation cycle. Cuttings were taken from superior trees and grafted to hardy rootstocks. These grafted trees, in turn, were set out to become the first commercial seed orchards. This marked the beginning of overcoming the dependence on the vagaries of nature by collection of wild seed. It also marked the beginning of the genetic improvement of forest crops, much as man has done with other agricultural crops for several thousands of years.

Trees, however, represent a far more difficult problem to the breeder than do annual crops such as corn or wheat. Depending on the species, it may take from 15 to 50 years for a new generation to produce seeds of its own. However, several generations of breeding are required to maximize genetic improvement. This produces a very serious handicap to the tree breeder. He must take cross pollinated seed from his first generation orchard and plant a certain amount of it in genetic test plots. The best trees from the $F_1$ generation are then selected and grafted for additional cross breeding experiments. Some of the seed from these matings must again be set out into genetic test plots and the best trees once more selected, with the cycle repeating itself about every 20 years using currently available methods.

Since the object of a forest tree breeding program is to be able to supply genetically superior seedlings by the hundreds of millions in the shortest time possible, it is critical to reduce the generation time of stock in the breeding program. Unless major reductions could be made, it was apparent that for many species the tree scientists working on improvement programs would not be alive to realize the fruits of their labors. The maximum benefits would also be denied to the public with an ever increasing need for wood fiber.

Approximately thirty species of gymnosperms, the so called softwoods, comprise the great bulk of the commercially important timber species useful for construction lumber. Among these are the pines which include loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertinana*), lodgepole pine (*Pinus contorta*); Douglas-fir (*Pseudotsuga mensiesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*), noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniana*), and Alaska yellow-cedar (*Chamaecyparis nootkatensis*), and Western larch (*Laryx occidentalis*).

This list is not intended to be all-inclusive of the commercially important softwood species. It does, however, include the major ones which are commercially harvested and are becoming subject to intensive silvicultural management. Several species might be singles out as being particularly important. These are the four so-called southern yellow pines, slash, longleaf, shortleaf, and loblolly; ponderosa pine; Western hemlock; and Douglas-fir. Of this last group, loblolly pine and Douglas-fir have been the subject of intensive tree improvement breeding programs.

The problem of inducing early flowering in tree breeding programs is not a new one nor is it limited to forest species. It is one that has been of concern to orchardists for at least a century and a half. T. A. Knight, in a paper published in 1820, observed that certain fruit trees can be made to flower at earlier ages by stem girdling (*Trans. Hort. Soc. London* 4:159-162). This procedure is used to the present day and is effective on certain gymnosperms as well as dicotyledon angiosperms.

R. M. Sachs, who cites Knight in a paper published in 1977, contemplates the biochemical mechanism of flowering induction (*Hort. Sci.* 12:220-222). He generally agrees with Knight and suggests that "a nutrient diversion hypothesis . . . may best account for promotion of flowering" by treatments that induce stress in the trees. By this he is referring to means that appear to switch nutrients away from promotion of vegetative growth to inducement of flowering.

J. A. Romberger and R. A. Gregory (*In Proc. 3rd North Amer. For. Biol. Workshop*, Colorado State Univ., Fort Collins, Colo., pp. 132-147. 1974.) believe that in woody trees there are a number of interrelated systems, all of which must be permissive if flowering is to occur. They ponder the conditions which cause apparently similar cell clusters to differentiate in one of several directions, e.g., male or female strobili or vegetative buds.

D. I. Jackson and G. B. Sweet, in what is basically a massive literature review published 1971, draw some conclusions on bud differentiation from a somewhat different viewpoint. (*Hort. Abstr.* 42:9-24). They note that in Pinus species primordium formation does not occur while extension growth is in active. In young trees, flowering is very infrequent and the trees are considered juvenile. They feel further that the route from "meristematic initials" to flowering buds is a long one that is "easily reversible in its early stages." Again, in Pinus, they state that either flowers, needle fascicles or branches may form in the axils of the scale leaves at nodes. They suggest that the first determination that takes place is between vegetative or floral growth. In the latter case sexual determination is a step which occurs even further downstream. These authorities suggest the term "phase change" for the transition time when trees change from an unfruiting juvenile to a fruiting adult or mature stage.

R. H. Zimmerman published a similar survey in 1973, although it was heavily directed to the problems of juvenility and flowering of fruit trees (Hort. Sci. 7(5):447-455). He did, however, deal somewhat with Pinus and concluded that juvenility was related to a number of factors which included photoperiod, temperature, water supply and nutrients. He noted that top working; i.e., grafting of a juvenile scion into a mature blossoming tree, was one means of inducing earlier male blossoms in pine. Zimmerman made a further statement which can only be bound to strike dismay into the hearts of tree breaders. This was his observation in regard to early flowering that different plant species respond to different treatments and there is little or no predictability from one species to another.

A paper published in 1977 by the present inventor (Greenwood, M. S., *In Proc. 3rd World Consultation on Forest Tree Breeding,* Canberra, Australia, CSRIO. FO-FTB--4/25) looked specifically at the problem of producing early flowering in loblolly pine (*Pinus taeda*). A number of treatments were found to be effective in induction of female flowering, e.g., pot culture, gibberellins, water stress, girdling, or some combination of these. None of these treatments were effective in inducing male flowering, however. Zimmerman's statement of unpredictability is well supported in this work. Ethrel (2-chloroethyl phosphonic acid) treatment is effective in inducing both male and female flowering in some species. The same was true for the gibberellin GA 4/7 which is known to increase both male and female flowering in Douglas-fir. Neither of these treatments were effective in promoting male flowering by *Pinus taeda*.

Accordingly, one object with the present invention is to provide an improved method of inducing juvenile male and female flowering in gymnosperms of the family Pinaceae.

A further object is to provide an effective method for inducing juvenile male flowering in species of the genus Pinus.

SUMMARY OF THE INVENTION

Briefly stated, this invention comprises a process for inducing early flowering, particularly male flowering, in juvenile phase forest species by altering the natural period of dormancy. This is achieved by providing conditions which alter the normal vegetative growth pattern to allow time for induction, differentiation and formation of sexual buds. The method comprises reducing both the temperature and photoperiod to the point that vegetative growth ceases during a period in which it would otherwise be active, but not to such an extreme that the tree falls into a condition of full dormancy. This quiescent period, or resting state, is preferably induced after a period in which vegetative growth is encouraged beyond the normal dormancy time by providing favorable conditions of temperature and photoperiod. The method is also effective under conditions in which vegetative growth is terminated early in the season, before the time at which it would normally cease. After sexual buds have formed, the trees are maintained in an environment which permits flowering to occur and normal growth to resume.

BRIEF DESCRIPTION OF THE DRAWINGS

FIG. 1 shows the sequence of treatments and their effects on flowering on grafted juvenile scions of loblolly pine compared with the normal sequence of events during flowering of mature trees.

DESCRIPTION OF THE PREFERRED EMBODIMENTS

It seems quite probable that the inability of most species within the genus Pinus to flower for a number of years may be a direct or indirect consequence of the juvenile phase, during which reproductive competence cannot be easily expressed. Surprisingly, there is good evidence in the case of loblolly pine, at least, that it is reproductively competent even when very young. Apparently it fails to flower because the normal growth behavior of young trees does not allow enough time for differentiation of strobilus buds to occur. Young loblolly pine trees grow vegetatively for a much longer period during a given growing season than mature trees and, therefore, set a quiescent bud relatively late in the growing season. However, flower bud initiation and differentiation is a time consuming process which apparently requires earlier formation of a quiescent bud. The present method forces bud set in actively growing immature juvenile phase trees early in the growing season, so that quiescent buds form during late spring. Quite surprisingly, it has been found that both male and female strobili result from such buds. This has been best accomplished by prolonging vegetative growth through the winter, and then forcing bud set in the early spring by reducing temperature and photoperiod. By this method both male and female strobili have been induced on scion material as young as three years old from seed.

The reproductive competence of juvenile scions appears to be related to the induction of a quiescent bud which persists for several months during temperature and photoperiod conditions which are otherwise favorable for vegetative growth. In 19 year old loblolly pine seed orchard trees, which produce heavy crops of both male and female strobili, a quiescent bud is usually set in early July after elongation of a single two cycle flush which was performed in the previous growing season. Male strobilus primordia initiate in those buds during late July and females initiate in early August. They do not differentiate into recognizable reproductive structures until late September, however. Therefore, the normal time course of strobilus bud formation extends well over two months. During that time the bud remains enclosed in bud scales, and develops short shoots and lateral primordia, but no internode elongation occurs on any of the terminal or lateral buds until the following spring.

In contrast, young trees produce lateral primordia and short shoots which quickly begin to elongate internodes and complete their development. Three year old loblolly pine may sequentially produce as many as four temporary buds in one growing season. These begin to elongate almost immediately. The final quiescent bud that will over-winter is not formed until September. Therefore, lateral primordia which might be potentially reproductive may form too late in the growing season to allow the lengthy process of strobilis differentiation to be completed. In the present method the juvenile trees were induced to form a quiescent bud which persisted over two months during favorable spring growing conditions.

It thus appears that reproductive competence in juvenile trees is masked by bud set too late to permit the differentiation of reproductive structures. The transition to the adult reproductive phase, at least in loblolly pine, appears to be in part a function of what is apparently a loss of the ability to elongate several buds during the growing season. The critical event in the transition to the adult reproductive phase in loblolly pine, and possibly other temperate zone woody plants, seems to be the change in vegetative growth behavior that results in the formation of quiescent buds earlier in the growing season. It appears critical that this change must allow sufficient time for the slow process of initiation and differentiation of reproductive structures during good growing conditions. Whatever it is that causes phase change from juvenile to adult appears to act principaly on vegetative growth behavior and seems to only indirectly affect reproductive development. This belief is further supported by the observation that stimulation of vegetative growth by frequent watering and fertilization resulted in no female flowering and greatly reduced male flowering on two year old potted grafts of fifty to sixty year old mature scion material. These grafts were vegetatively more vigorous than similar grafts of the same clones which are simultaneously water stressed or shocked by reduced photoperiod and temperature. Ramets receiving these last two treatments formed a heavy crop of both male and female strobili.

EXAMPLE

Scions of two, four and six year old (from seed) plants representing six clones and two half sib families were grafted in April onto one year old root stock potted in a 2:1:1 mixture of sand:vermiculite:peat moss. They were top dressed with a timed release fertilizer. The ramets of each of the full sib families represent a clone of a single tree from within that family. Grafts of each of the half sib families do not represent a clone but result from scions from different seedlings within that family. All the grafted ramets were kept in a greenhouse under natural day length until early October. At that time, the ramets from each family and clone were divided into two equal blocks. One block was moved outdoors at Hot Springs, Arkansas while the other was kept in the greenhouse, with day temperature maintained at 20°–25° C. and night temperature 8°–15° C. Daylength was extended to 20 hours using 80 $\mu W/cm^2$ of incandescent light. In February of the following year, the indoor block, which was still actively growing, was transferred to an unheated greenhouse with no supplemental lighting (see FIG. 1). Temperatures and photoperiod experienced by the indoor block for four weeks before and after their transfer are summarized in Table 1.

Table 1

| Average Weekly Maximum and Minimum Temperature and Photoperiod Before and After Transfer to Unheated Greenhouses | | | |
|---|---|---|---|
| Week of: | Min. Temp. | Max. Temp. | Photoperiod, hours |
| Jan. 18 | 8° C. | 23° C. | 20 |
| Jan. 25 | 9 | 27 | 20 |
| Feb. 1 | 10 | 28 | 20 |
| Feb. 8 | 11 | 26 | 20 |
| Feb. 14 | Moved to unheated greenhouse | | |
| Feb. 15 | 1° C. | 20° C. | 10.0 |
| Feb. 22 | 7 | 24 | 10.3 |
| March 1 | 3 | 19 | 10.7 |
| March 8 | 7 | 25 | 11.0 |

Experimental work summarized on this table was doneat Hot Springs, Arkansas.

Night temperatures of the block in the unheated greenhouse were near freezing and the natural photoperiod was approximately 10 hours. Under these conditions the ramets set quiescent buds shortly after their transfer to the unheated greenhouse and practically no elongation was observed until mid-May, over two months later. In contrast, ramets from the control block moved outdoors in October began to elongate vigorous vegetative flushes in mid-March of the following year.

In mid-May receptive female conelets were observed on ramets of the indoor block. These continued to emerge until mid-August, at which time male strobilus buds began to appear through mid-September. Both male and female strobili occurred on all ages of scion material and there was no significant difference in the frequency of male and female flowering between three, five and seven year old scions. Ramets from all six clones and three half sib families produced male strobili, while ramets from all six clones and one of three sib families produced female strobili. Forty-seven percent of the ramets produced male strobili while 29 percent produced female strobili. No male strobili were found on any trees of the outdoor block and only a single female cone was observed.

Table 2

Male and Female Strobilus Production by Ramets Grafted in Spring

| Scion Source* | Scion Age | Indoor Block | | | Outdoor Block | | |
|---|---|---|---|---|---|---|---|
| | | Total # Ramets | # Ramets with ♀ | # Ramets with ♂ | Total # Ramets | # Ramets with ♀ | # Ramets with ♂ |
| A × op | 3 | 5 | 0 | 3 | 6 | 0 | 0 |
| B × op | 3 | 6 | 2 | 3 | 5 | 0 | 0 |
| C × op | 3 | 6 | 0 | 2 | 4 | 0 | 0 |
| D × E | 5 | 6 | 2 | 1 | 8 | 0 | 0 |
| F × G | 5 | 7 | 3 | 7 | 7 | 0 | 0 |
| H × I | 7 | 15 | 3 | 1 | 16 | 0 | 0 |
| C × J | 7 | 16 | 7 | 8 | 12 | 0 | 0 |
| K × J | 7 | 15 | 5 | 6 | 11 | 0 | 0 |
| K × L | 7 | 10 | 3 | 9 | 16 | 1 | 0 |
| Totals | | 86 | 25 | 40 | 85 | 1 | 0 |
| % Flowering | | — | 29 | 47 | — | 1 | 0 |

*The letter designations represent genetic families; scions come from a single offspring tree within each mating. Op indicates open pollinated, half-sib families; scions come from different trees within each family.

Some species of the Pinaceae may require a short period of sub-freezing weather after bud formation is completed before active growth will be resumed. This is not the case with loblolly pine, however.

It can thus be seen that by causing termination of vegetative growth and forcing bud set while there is still a favorable period short of full dormancy for bud differentiation and development, both male and female sexual buds can be successfully induced on juvenile scions. This makes collection of seed for further breeding work possible as much as 10 to 15 years earlier than would otherwise be the case if natural maturation through the juvenile phase were allowed to occur. It also permits the tree improvement scientist to work through a series of perhaps 6 to 10 generations during his professional career when, otherwise, he would be limited to one or two.

This method is believed to be useful on all members of the family Pinaceae that experience a juvenile phase. It is regarded of particular value for the important and genetically close Southern yellow pines *P. taeda, P. elliotii, P. palustris, P. echinata,* and for ponderosa pine, *P. ponderosa.*

While a preferred embodiment of the present invention has been described, it is to be understood that many changes and modifications may be made without departing from the scope of the invention. All such modifications are intended to be included within the scope of the following claims.

I claim:
1. A method of causing early flowering in the juvenile phase of southern yellow pine trees comprising:
   a. placing actively growing trees under conditions of reduced temperature and photoperiod sufficient to arrest said active growth and induce bud set in order to bring the trees into a resting state,
   b. providing an environment for the resting trees in which the temperature and photoperiod conditions would favor vegetative growth so as to allow male and female sexual buds to form during the resting period, and
   c. maintaining the trees in said environment so that male and female strobili flush and the trees resume natural growth.
2. The method of claim 1 where the trees are yellow pines of the species *P. taeda, P. elliottii, P. palustris,* and *P. enchinata.*
3. The method of claim 2 where the trees are within the species *P. taeda.*
4. The method of claim 1 where active growth is forced through the fall and early winter months by artificially increasing temperature and photoperiod and growth is then arrested in later winter by exposing the plants to essentially ambient conditions.
5. The method of claim 4 where the active growth photoperiod is maintained at about 20 hours daily from October until mid-February, day temperatures are held at least at 20° C. and night temperatures are not permitted to fall below about 8° C.
6. The method of claim 4 where the trees are yellow pines of the species *P. taeda, P. elliottii, P. palustris,* and *P. echinata.*
7. The method of claim 6 when the trees are within the species *P. taeda.*

* * * * *

UNITED STATES PATENT AND TRADEMARK OFFICE
CERTIFICATE OF CORRECTION

PATENT NO. : 4,199,897
DATED : April 29, 1980
INVENTOR(S) : Michael S. Greenwood It is certified that error appears in the above-identified patent and that said Letters Patent are hereby corrected as shown below:

In column 1, line 14 "the" should be "this"
In column 1, line 29 "recognized" should be "unrecognized"

Signed and Sealed this

Twenty-second Day of July 1980

[SEAL]

Attest:

SIDNEY A. DIAMOND

Attesting Officer

Commissioner of Patents and Trademarks